(12) United States Patent
Berard et al.

(10) Patent No.: US 7,105,805 B2
(45) Date of Patent: Sep. 12, 2006

(54) APPARATUS AND A METHOD FOR CHARACTERIZING MULTIPHASE EFFLUENTS

(75) Inventors: Michel Victor Berard, Al-Khobar (SA); Gerard Segeral, Gif sur Yvette (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 234 days.

(21) Appl. No.: 10/450,628

(22) PCT Filed: Dec. 6, 2001

(86) PCT No.: PCT/EP01/14473

§ 371 (c)(1),
(2), (4) Date: Oct. 24, 2003

(87) PCT Pub. No.: WO02/50522

PCT Pub. Date: Jun. 27, 2002

(65) Prior Publication Data

US 2004/0046115 A1    Mar. 11, 2004

(30) Foreign Application Priority Data

Dec. 19, 2000 (FR) .................................. 00 16613

(51) Int. Cl.
*G01V 5/00* (2006.01)

(52) U.S. Cl. ..................................................... 250/256

(58) Field of Classification Search ................. 250/256
See application file for complete search history.

(56) References Cited

U.S. PATENT DOCUMENTS

| | | | | |
|---|---|---|---|---|
| 4,490,609 A | * | 12/1984 | Chevalier | ................. 250/269.1 |
| 4,511,799 A | * | 4/1985 | Bjorkholm | .................. 250/367 |
| 5,025,160 A | * | 6/1991 | Watt | ......................... 250/356.1 |
| 6,389,908 B1 | * | 5/2002 | Chevalier et al. | .......... 73/861.63 |

FOREIGN PATENT DOCUMENTS

| | | | |
|---|---|---|---|
| GB | 2325735 A | * | 12/1998 |
| WO | WO 94/25859 | | 11/1994 |
| WO | WO 9910712 A1 | * | 3/1999 |

OTHER PUBLICATIONS

International Search Report dated Jun. 13, 2002 from PCT/EP01/14473, not a publication.

* cited by examiner

*Primary Examiner*—Constantine Hannaher
(74) *Attorney, Agent, or Firm*—Victor H. Segura; Brigitte L. Echols

(57) ABSTRACT

An apparatus for characterizing an effluent formed by a multiphase fluid mixture is described, said apparatus comprising a source emitting gamma rays at a plurality of energy levels through said effluent towards a detector block that takes account of the photons it receives as a consequence thereof to deduce therefrom the attenuation of said rays by said effluent. The detector block includes a filter for selectively detecting the photons it receives at a first energy level and at a second energy level, said first and second levels being predetermined amongst the energy levels of radiation from the source.

34 Claims, 1 Drawing Sheet

APPARATUS AND A METHOD FOR CHARACTERIZING MULTIPHASE EFFLUENTS

Figure 1:
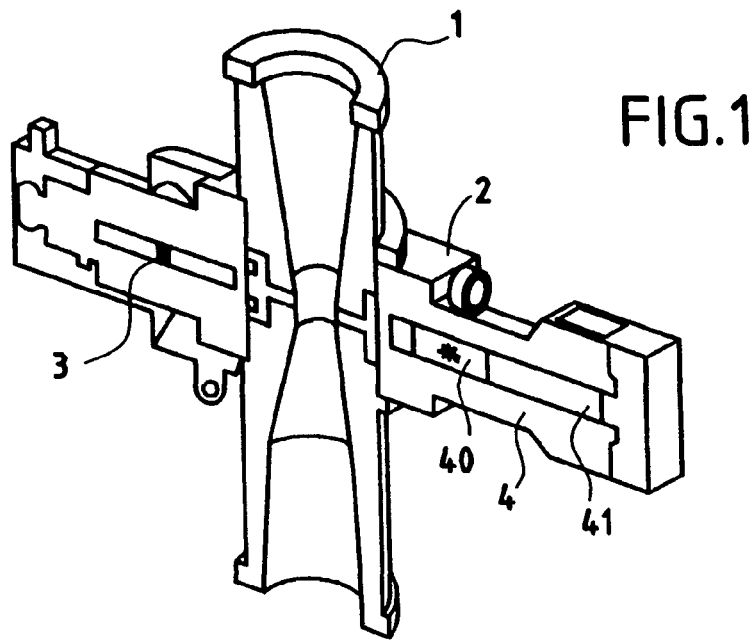

The invention relates to apparatus and to a method for characterizing multiphase effluents. A particular application of the invention lies in taking measurements concerning the composition of effluents coming from oil wells, which effluents are constituted by multiphase fluids typically comprising three phases: two liquid phases, namely crude oil and water, and a gas phase which is based on hydrocarbons.

In the oil industry, the traditional practice for characterizing the composition of multiphase effluents consists in separating the effluent into its component phases and in measuring the phases as separated in this way. However, that technique requires separators to be installed on site, even though separators are pieces of equipment that are expensive and voluminous, and when testing wells that method also requires additional pipes.

Numerous proposals have been put forward to develop techniques making it possible to avoid making use of such separators. A description of such developments can be found in the publication SPE 28515 (SPE Annual Technical Conference, New Orleans, Sep. 25–28, 1994) by J. Williams entitled "Status of multiphase flow measurement research".

French patent FR 2 764 065 describes a method of characterizing an oil well effluent directly inside the production tubing without it being necessary to perform separation. In that method, a gadolinium 153 source is used to emit gamma rays into the effluent at a first energy level of about 100 kilo electron-volts (keV), and also at a second energy level of about 40 keV, and the attenuation of the gamma rays at each of those two levels is measured after the rays have passed through the effluent. The measurements taken make it possible to determine the oil/water/gas fractions in the effluent. Combining those measurements with measurements from a flowmeter makes it possible to deduce production for each of the three phases.

However, since the lifetime (period) of gadolinium 153 is short (less than one year) it is of interest for taking measurements over a short duration such as periodic measurements in oil wells, but it is unsuitable for taking measurements on a permanent or semipermanent basis. When measurements are taken by tools that are fixed in non-removable manner in or on a well, it is necessary to use a source whose lifetime is long enough to ensure that the tool continues to operate throughout the lifetime of the well, without it being necessary to change the source.

Barium 133 has already been used as another source for emitting gamma rays and it has the advantage of a lifetime that is longer. That source therefore makes it possible to implement permanent measurements. In conventional manner, such measurements are performed by measuring the attenuation of gamma rays at a first energy level of 32 keV and at a second energy level of 356 keV. In such applications, the energy of the nuclear instrumentation of the tool is stabilized on the peak at 356 keV, i.e. the peak in the photons received by the detector block at the corresponding energy level is calibrated so as to enable said photons to be counted accurately. That gives rise to various drawbacks. Firstly, the energy peak corresponding to radiation at 356 keV does not have the appearance of a Gauss curve. The distribution of the curve relative to its high point is very broad and highly asymmetrical due to the presence of other energy peaks (276 keV, 303 keV, and 384 keV) that are not fully resolved by the scintillator crystal of a detector. That gives rise to the major drawback of making it difficult to stabilize the detector, so stabilization is only approximate. Secondly, the photons emitted at 356 keV tend to deposit only a fraction of their energy in the detector crystal, thus disturbing measurements at lower energy.

An object of the invention is thus to remedy those drawbacks by proposing apparatus and a method for characterizing oil well effluent in such a manner that the fractions and the densities of the phases in said effluent are determined in particularly reliable manner.

To this end, the invention provides apparatus for characterizing an effluent formed by a multiphase fluid mixture, said apparatus comprising a source emitting gamma rays at a plurality of energy levels through said effluent towards a detector block that takes account of the photons it receives as a consequence thereof to deduce therefrom the attenuation of said rays by said effluent. According to the invention, the detector block includes a filter for selectively detecting the photons it receives at a first energy level and at a second energy level, said first and second levels being predetermined amongst the energy levels of radiation from the source.

This solution is particularly advantages since the apparatus makes it possible to decrease the number of photons that are uselessly detected by the detector block, thereby significantly increasing the efficiency of the measurements. This decrease makes it possible to minimize corrections for pile-ups, i.e. the addition effects between two photons which are detected simultaneously at different energy levels so that they are taken to be constituted by a single photon at a higher energy level. This solution also makes it possible to decrease the dead time that corresponds to the time during which the detector block is unavailable between detecting the arrival of one photon and actually allocating a certain energy level thereto. These two improvements increase the accuracy with which attenuation measurements are performed for given source activity or they make it possible to increase source activity so as to reduce statistical error. Finally, by not responding to a large fraction of the photons that are emitted at other energy levels, the apparatus of the invention makes it possible to decrease significantly the measurement errors encountered with apparatuses known in the prior art.

In a preferred embodiment of the invention, the filter comprises a scintillator crystal whose dimensions are such that said crystal mainly detects photons that are emitted at said first and second energy levels.

This embodiment is advantageous since it makes it possible in a manner that is very simple and low in cost to implement the function of discriminating between different photon energy levels in the apparatus of the invention. The larger the dimensions of the scintillator crystal, the more said crystal can detect high energy photons, so a consequential adaptation of said dimensions thus makes it possible quite simply to count only a fraction of said photons received by the detector block. With the apparatus of the invention, it is possible to detect mainly those photons which are emitted at the lowest energy levels while detecting only a smaller fraction of the photons received at higher energy levels.

In an advantageous embodiment of the invention, the gamma ray emitting source comprises barium 133.

This solution is advantageous since by using a source having a lifetime that is long it enables the apparatus to be used for permanently measuring the composition of an effluent, e.g. down an oil well, on an inhabited platform, or at the bottom of the sea.

In a preferred embodiment of the invention, the first energy level is situated substantially at 32 keV, and the second energy level is situated substantially at 80 keV. In this preferred example, the apparatus of the invention also includes a stabilization loop locked on the first and/or the second energy level.

These two energy levels are preferred because photon counting turns out to be more accurate at these levels. The decrease in the quantity of high energy photons taken into account reduces the risks of pile-ups and reduces dead times. In addition, since the stabilization loop is locked on one of these two energy levels, or on both of them, the fact that they are close to each other makes it possible to minimize errors in allocating a photon to one or other of the levels during counting. Finally, the energy peak corresponding to radiation at 80 keV has the appearance of a Gaussian curve with distribution relative to its high point that is narrow, thereby guaranteeing accurate calibration in terms of energy received and photon allocation to a particular spectrum line. The same applies to the peak at 32 keV.

The invention also provides a method of characterizing an effluent formed by a multiphase fluid mixture, in which method:

gamma rays are emitted into said effluent by means of a gamma ray emitting source at a plurality of energy levels;

the photons received from said source after passing through said effluent are filtered by means of a detector block so as to detect selectively the photons which correspond to gamma rays at a first energy level and at a second energy level, said first and second energy levels being predetermined amongst the energy levels at which the source radiates; and the attenuation of the gamma rays at said first and second energy levels is measured on the basis of the count rate corresponding to the number of photons detected after filtering so as to deduce therefrom the fractions of the various phases in said effluent.

Figure 2:
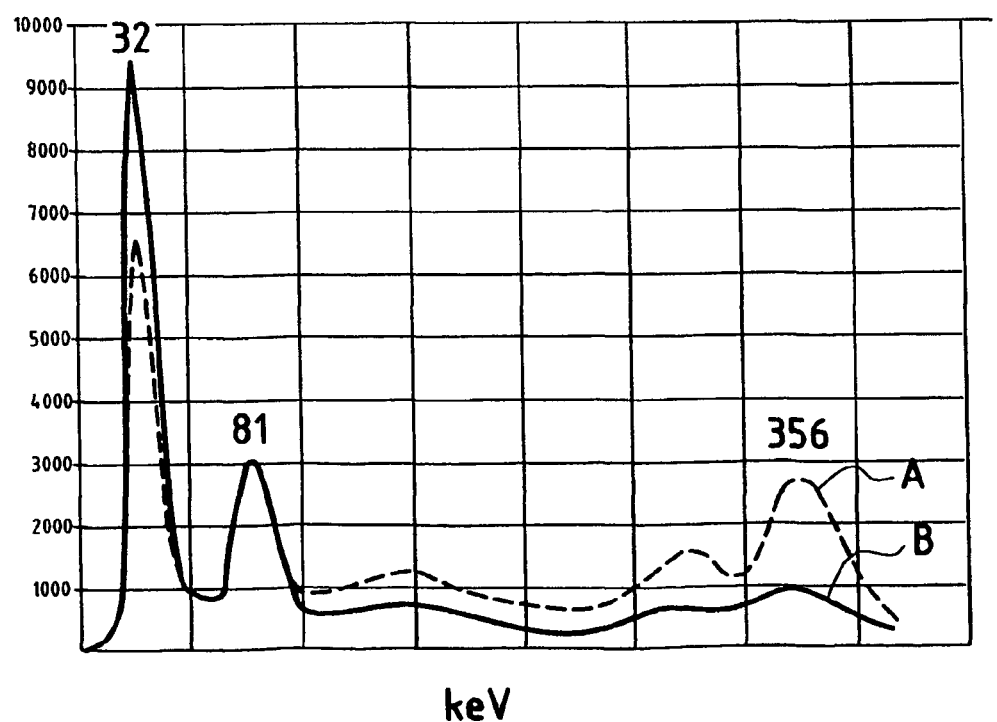

Other advantages and characteristics of the invention become clear from the following description given by way of example and made with reference to the accompanying drawing, in which:

FIG. 1 is a diagrammatic view in section and in perspective of a piece of apparatus in accordance with the invention; and FIG. 2 shows two photon detection spectra, one of which is obtained by means of apparatus of the invention.

FIG. 1 shows a section of pipe 1 in which a multiphase fluid mixture flows. By way of example, this pipe is situated in an oil well and the multiphase fluid comprises water, oil, and gas. Apparatus 2 of the invention is installed on said pipe. The apparatus comprises a source 3 and a detector 4 placed on opposite sides of the pipe 1, the pipe being provided with "windows" of material that is a poor absorber of photons at the energies under consideration. In the embodiment shown, the source 3 comprises barium 133 which produces gamma rays at various energy levels: 30 keV, 80 keV, 276 keV, 303 keV, 356 keV, and 384 keV. However, any other chemical or electronic gamma ray source could be used.

In the advantageous embodiment of the apparatus of the invention, as shown in FIG. 1, the section of pipe 1 includes a converging Venturi. The source 3 and the detector 4 are situated on either side of the throat of the Venturi, i.e. the narrowest portion thereof. This enables measurements to the composition of the effluent to be coupled with measurements of its flow rates, e.g. using the method described in French patent No. FR 97/10648.

The detector 4 comprises a scintillator crystal 40, such as an NaI crystal, together with a photomultiplier 41. In the detectors known in the prior art, the photomultiplier 41 takes account, amongst other things, of photons corresponding to two energy levels referred to as a "high" energy level and as a "low" energy level, corresponding substantially to 32 keV and to 356 keV, respectively. These energy levels are such that the "high energy" count rate is responsive essentially to the density of the fluid mixture while the "low energy" count rate is also sensitive to the composition of the liquid mixture, thus making it possible to determine the water content of the effluent. However, the scintillator crystal is such that all of the photons emitted by the source 3 are detected and taken into consideration, thereby giving rise to errors in measuring the energy levels which are particularly intended for measuring the composition of the effluent.

The scintillator crystal 40 of the invention is such that, on the contrary, only a fraction of the photons emitted by the source 3 are detected. The length d of the crystal 40 is previously determined so that this crystal mainly detects photons having an energy level that is substantially less than or equal to 80 keV, the major fraction of photons at higher energy levels passing through the crystal without being detected. As a result, the photomultiplier 41 takes account only of "low" energy level photons corresponding substantially to 30 keV and of "high" energy level photons corresponding substantially to 80 keV.

This selective detection is particularly advantageous because it decreases the total number of photons that are detected and therefore decreases the errors that are statistically inherent to such counting. The apparatus of the invention preferentially detects useful photons (those at low energy), thereby reducing errors, in particular those due to pile-ups and also reducing the dead time of the detector block. Thus, errors are no longer induced by the sheer number of photons to be detected since overall this number is reduced.

For characterizing oil effluent, the "high" energy level presents a remarkable property whereby the gamma ray attenuation coefficient per unit mass is substantially the same at this level for fresh water, salt water, and oil. As a result, the "high energy" attenuation makes it possible to determine the density of the mixture without it being necessary for this purpose to perform any auxiliary measurements (attenuation coefficients and densities) in order to determine the individual phases of the effluent.

At this energy level, the attenuation A as measured by the detector 21 can be expressed by the following relationship:

$$A = D_v \cdot v_m \cdot \rho_m \quad [1]$$

where $D_v$ is the distance traveled through the fluid, i.e., in this case, the diameter of the section of pipe 1, where $v_m$ is the attenuation coefficient per unit mass, and $\rho_m$ is the density of the multiphase mixture.

Since the attenuation coefficients per unit mass of water and oil have values that are substantially identical at the above-mentioned energy level, and since the contribution of gas is negligible because of its very low density, the attenuation coefficient per unit mass $v_m$, and thus the product $D_v \cdot v_m$ that appears in equation [1] can be considered as being substantially constant, and independent of the densities of the oil and water phases. Under such conditions, the "high energy" attenuation $A_{he}$ is a highly advantageous indicator of the density $\rho_m$ of the mixture.

The photomultiplier 41 of the detector block 4 of the invention also has a stabilization loop set to the "high"

energy level at 80 keV. This stabilization loop serves to enable the photomultiplier to allocate an energy level to a photon detected by the scintillator crystal so as to enable the photon to be counted appropriately. This setting of the photomultiplier on the 80 keV peak generates the calibration enabling other photons to be allocated to the other energy levels that correspond to them. With apparatus of the invention, the stabilization loop is particularly effective, for several reasons.

Firstly, as can also be seen in FIG. 2, the peak corresponding to the 80 keV level is in the form of a very narrow Gaussian curve. It is thus easier to stabilize apparatus on this narrow detection range rather than on a broader range as is necessary with the 356 keV peak which has the form of a much wider Gaussian curve. Thereafter, since the "high" energy level and the "low" energy level are closer together, it is also easy to guarantee minimum deviation of the stabilization for the "low" energy level.

In another embodiment of the apparatus of the invention, a second stabilization loop can advantageously be included based on the "low energy" peak, thereby further increasing accuracy of counting. The count rates at the two energy levels in question thus turn out to be very reliable.

To illustrate the advantages of the apparatus of the invention, FIG. 2 shows two spectra corresponding to the count rates of two detector blocks. Both spectra are normalized on the 80 keV peak for comparison purposes. The first curve A corresponds to the spectrum obtained with a device whose stabilization loop is locked on the 80 keV energy level and for which the length d of the scintillator crystal is large, being about 1 inch (25.4 mm). The second curve B, corresponds to the spectra obtained from apparatus of the invention in which the stabilization loop is indexed on the 80 keV energy level and for which the length d of the scintillator crystal is short: about half an inch (12.7 mm). On comparing these two curves, it can clearly be seen that the amplitude of the peak corresponding to the 356 keV level is much lower in curve B than in curve A, simply because the apparatus of the invention detects very few photons at this energy level. The shaded portion corresponds to the increase in count rate obtained by the detector block of curve B compared with the count rate obtained by the detector block of curve A. It can be seen that curve B is low at energies above 100 keV whereas the height of curve A at such energy levels is higher. The greater height beneath curve A comes from the way in which the measurements are so to speak "polluted" by the known Compton phenomenon effected by the 356 keV photons (a fraction of their energy is detected while the remaining fraction is detected as being at a lower level and therefore appears in the graph). As a result, curve B presents a spectrum whose appearance is more representative of the photons that are genuinely useful at the 80 keV and 30 keV levels.

With the apparatus of the invention, the method of determining the multiphase composition of an effluent turns out to be particularly simple and reliable. This composition is determined using the following principles: if the attenuation of the gamma rays induced by each of the components taken separately at 80 keV and at 30 keV and if the density of each of these components are all known, then the attenuation of gamma rays at 80 keV characterizes the density and thus the gas fraction in the multiphase effluent and combining data at 80 keV and at 30 keV for said mixture characterizes the water fraction in the effluent.

This calculation can be presented in matrix form as follows:

$$\begin{bmatrix} A^H \\ A^L \\ 1 \end{bmatrix} = \begin{bmatrix} A_o^H & A_w^H & A_g^H \\ A_o^L & A_w^L & A_g^L \\ 1 & 1 & 1 \end{bmatrix} = \begin{bmatrix} \alpha_o \\ \alpha_w \\ \alpha_g \end{bmatrix}$$

where the oil, water, and gas fractions are the unknowns $\alpha_i$, where H represent the "high" energy level, L represents the "low" energy level, o represents the oil phase, w represents the water phase, and g represents the gas phase.

To determine the attenuations of the various components and of the mixture at 30 keV and at 80 keV, the method of the invention thus consists in using the source 3 to emit gamma rays through the section of pipe 1 towards the detector block 4. Thereafter, the scintillator crystal 40 of the detector block detects photons that correspond mainly to the 30 keV and 80 keV energy levels after they have passed through the effluent, with the length d of said crystal being insufficient to retain all of the high energy photons. Comparing the count rates obtained in this way with those obtained when the section of pipe is empty makes it possible to deduce the attenuation that is due to the multiphase mixture, and finally to deduce the composition of said mixture.

The method and apparatus of the invention thus makes it possible to obtain photon count rates that are particularly reliable so as to provide the composition of a multiphase fluid mixture. When the source which emits the gamma rays at a plurality of energy levels is barium 133, then the apparatus of the invention can be used in applications for permanently measuring the composition of an effluent, e.g. flowing in the downhole pipes of an oil well or in a pipe situated on the seabed or at the surface.

The invention claimed is:

1. Apparatus for characterizing an effluent formed by a multiphase fluid mixture, comprising:
   a source emitting gamma rays at a plurality of energy levels through the effluent so as to be attenuated thereby; and
   a detector block comprising a photomultiplier, wherein the detector block:
      is positioned so as to receive photons from the source that have passed through the effluent;
      includes a filter for simultaneously capturing photons at first and second energy levels, the first and second energy levels photons passing through the filter and said first and second energy levels being selected from the plurality of energy levels of gamma rays emitted from the source;
      deduces the attenuation of the gamma rays by the effluent by taking into account the received photons at the first and second energy levels; and
      ensures that the photomultiplier takes account only of the first and second energy levels.

2. Apparatus as claimed in claim 1, wherein the filter comprises a scintillator crystal whose dimensions are such that the crystal mainly detects photons that are emitted at the first and second energy levels.

3. Apparatus as claimed in claim 2, wherein the scintillator crystal has a length selected to detect photons having energy levels not greater than a higher of the first and second energy levels.

4. Apparatus as claimed in claim 3, wherein the scintillator crystal has a length selected so that a major fraction of photons having energy levels substantially higher than the higher of the first and second energy levels are not detected.

5. Apparatus as claimed in claim 2, wherein the scintillator crystal has a length of not more than half an inch.

6. Apparatus as claimed in claim 1, wherein the gamma ray emitting source comprises barium 133.

7. Apparatus as claimed in claim 1, wherein the first energy level is situated substantially at 30 keV and the second energy level is situated substantially at 80 keV.

8. Apparatus as claimed in claim 1, further comprising a stabilization loop locked on the first energy level and/or a second stabilization loop locked on the second energy level.

9. Apparatus as claimed in claim 1, further comprising a stabilization loop locked on the second energy level.

10. Apparatus as claimed in claim 1, further comprising a first stabilization loop locked on the firm energy level and a second stabilization loop locked on the second energy level.

11. Apparatus as claimed in claim 1, further comprising a converging Venturi coupled to the source and the detector.

12. Apparatus as claimed in claim 1, wherein the multiphase mixture comprises oil, water, and gas.

13. Apparatus as claimed in claim 1, wherein the detector block provides first and second count rates corresponding to a number of photons detected at the first and second energy levels respectively.

14. A system for use in measuring flows from wells comprising:
  a pipe carrying an effluent flow from a well and adapted to receive a source and a detector block;
  a source, adapted to be coupled to the pipe, emitting gamma rays at a plurality of energy levels trough the affluent so as to be attenuated thereby; and
  a detector block comprising a photomultiplier, wherein the detector block:
    is positioned so as to receive photons from the source that have passed through the effluent;
    includes a filter, adapted to be coupled to the pipe, for simultaneously capturing photons at first and second energy levels, the first and second energy levels photons passing through the filter and said first and second energy levels being selected from the plurality of energy levels of gamma rays emitted from the source;
    deduces the attenuation of the gamma rays by the effluent by taking into account the received photons at the first and second energy levels; and
    ensures that the photomultiplier takes account only of the first and second energy levels.

15. A system as claimed in claim 14, wherein the pipe comprises a Venturi.

16. A system as claimed in claim 15, wherein the pipe is adapted to receive the source and detector block at the throat of the Venturi.

17. A system as claimed in claim 15, further comprising a plurality of pipes, each connected to a well so as to carry the effluent therefrom.

18. A system as claimed in claim 15, wherein the effluent flow comprises a mixture of oil, water and gas.

19. A system as claimed in claim 15, wherein the filter comprises a scintillator crystal whose dimensions are such that the crystal mainly detects photons that are emitted at the first and second energy levels.

20. A system as claimed in claim 19, wherein the scintillator crystal has a length selected to detect photons having energy levels at least equal to a higher of the first and second energy levels.

21. A system as claimed in claim 20, wherein the scintillator crystal has a length selected so that a major fraction of photons having energy levels substantially higher than the higher of the first and second energy levels are not detected.

22. A system as claimed in any of claims 19, wherein the scintillator crystal has a length of not more than half an inch.

23. A system as claimed in claim 15, wherein the gamma ray emitting source comprises barium 133.

24. A system as claimed in claim 15, wherein the first energy level is simulated substantially at 30 keV and the second energy level is situated substantially at 80 keV.

25. A system as claimed in claim 15, further comprising a stabilization loop locked on the first energy level and/or a second stabilization loop locked on the second energy level.

26. A system as claimed in claim 15, further comprising a stabilization loop locked on the second energy level.

27. A system as claimed in claim 15, further comprising a first stabilization loop locked on the first energy level and a second stabilization loop locked on the second energy level.

28. A system as claimed in claim 15, wherein the detector block provides first and second count rates corresponding to a number of photons detected at the first and second energy levels respectively.

29. A method of characterizing an effluent formed by a multiphase fluid mixture, comprising:
  emitting gamma rays into the effluent by means of a gamma ray emitting source at a plurality of energy levels;
  filtering photons resulting from emission of the gamma rays through the effluent by means of a detector block so as to simultaneously retain photons it receives both at a first energy level and at a second energy level, the firs and second energy levels being selected from the plurality of energy levels of the source; the filtering step being made such that the first and second energy levels photons pass through the filtering;
  detecting only the first and second enemy levels by means of a photomultiplier; and
  measuring attenuation of the gamma rays at the first and second energy levels on the basis of count rates corresponding to the number of photons detected after filtering so as to deduce therefrom fractions of various phases in the effluent.

30. A method as claimed in claim 29, wherein the filtering is performed to detect photons having energy levels not greater than a higher of the first and second energy levels.

31. A method as claimed in claim 29, wherein the filtering is performed so that a major fraction of photons having energy levels substantially higher than a higher of the first and second energy levels are not detected.

32. A method as claimed in claim 29, wherein the first energy level is situated substantially at 30 keV and the second energy level is situated substantially at 80 keV.

33. A method as claimed in claim 29 wherein the multiphase mixture comprises oil, water, and gas.

34. A method as claimed in claim 29, further comprising determining a density of the multiphase mixture.

* * * * *